(12) United States Patent
Chang

(10) Patent No.: US 8,562,561 B2
(45) Date of Patent: Oct. 22, 2013

(54) SAFETY SYRINGE WITH RETRACTABLE ROTATION

(76) Inventor: Shu-Ming Chang, Nantou (TW)

( * ) Notice: Subject to any disclaimer, the term of this patent is extended or adjusted under 35 U.S.C. 154(b) by 142 days.

(21) Appl. No.: 13/158,436

(22) Filed: Jun. 12, 2011

(65) Prior Publication Data

US 2012/0226241 A1    Sep. 6, 2012

(30) Foreign Application Priority Data

Mar. 2, 2011 (CN) .......................... 2011 1 0050259

(51) Int. Cl.
*A61M 5/00* (2006.01)

(52) U.S. Cl.
USPC ............................ 604/110; 604/228; 604/240

(58) Field of Classification Search
USPC .................. 604/110, 218, 228, 240, 242, 243
See application file for complete search history.

(56) References Cited

U.S. PATENT DOCUMENTS

| 4,888,002 | A | * | 12/1989 | Braginetz et al. | ............. 604/195 |
| 2003/0212366 | A1 | * | 11/2003 | Bang | ............................. 604/196 |
| 2006/0189935 | A1 | | 8/2006 | Janek et al. | |
| 2010/0286610 | A1 | | 11/2010 | Chang | |

* cited by examiner

*Primary Examiner* — Emily Schmidt
(74) *Attorney, Agent, or Firm* — Chun-Ming Shih

(57) ABSTRACT

A safety syringe with retractile rotation is disclosed. The plunger is capable of rapidly embedding with and positioning at the needle set, the next step of the retractile movement to retract the needle is easily processed by a user, and the needle set is firmly assembled and positioned at the open end of the barrel so as to not easily result an unpredictable phenomenon, such as deteriorating the suitability between the needle set and the barrel to result the needle set indentation and leakage when injecting from a sharp raise in temperatures, or overtightening the needle set and the barrel to result the needle and the needle set incapable of retracting in the barrel from the sharp fall of temperature. Furthermore, this invention is capable of achieving one hand operation with safety, improving environmental protection quantity, and easy use for retracting the needle.

10 Claims, 9 Drawing Sheets

SAFETY SYRINGE WITH RETRACTABLE ROTATION

FIELD OF THE INVENTION

The present invention generally relates to a safety syringe with retractile rotation, and more particularly to a needle set capable of firmly positioning at an open end of a barrel and rotating by embedding with the barrel.

BACKGROUND OF THE INVENTION

The traditional syringe comprises an injecting needle but without any safety device. It is able to reuse and easily result in drug and blood contamination. In addition, the exposed needle is further easily stabbing medical personnel and cleanup personnel to make the infectious disease be infected much more. In accordance with the problems of the traditional syringe, how to develop a syringe to prevent from reusing and making secondary contamination is expected.

The recently retractile safety syringe is fastened at the open end of the barrel tightly. It is easily resulting from outside temperature, such as deteriorating the suitability between the needle set and the barrel to result the needle set indentation and leakage when injecting from a sharp raise in temperatures, or overtightening the needle set and the barrel to result the needle and the needle set incapable of retracting in the barrel from the sharp fall of temperature. Therefore, the quality control of the syringe is failed and further the yield rate is decreased.

SUMMARY OF THE INVENTION

An objective of this invention is providing a safety syringe with retractable rotation, which is capable of obviously improving the suitability between the needle set and the barrel, easily making the retractable movement for a user, so as to achieve one hand operation with safety and further to improve the environmental protection quantity.

To achieve above objectives, a safety syringe with retractable rotation is disclosed and comprises a barrel, having a receiving cavity formed in the barrel, at least one stopper arranged at an open end of the receiving cavity, and at least one guiding pressure plate arranged at a tail end of the barrel, wherein a limit groove of each guiding pressure plate is arranged corresponding to and toward the inside of the receiving cavity; a needle set, limited at the open end of the barrel and including a rotating member and a stopping member engaged with each other, wherein an auto deflection device is disposed between the rotating member and the stopping member, and the auto deflection device is having a rotated portion arranged inside the rotating member and a non-circular groove arranged at a predetermined position inside the stopping member, and an embedding portion is arranged at an end of the rotating member relative to the rotated portion, wherein at least one L-shaped groove is arranged at an outer ring edge of the rotating member for limiting or non-limiting the stopper of the barrel, and an assembling member is arranged at a rear end of the rotating member for embedding with the rotating member; and a plunger, having at least one radial rib arranged at outer edge, wherein the radial rib is guided by the limit groove of the guiding pressure plate and formed linear track-like, wherein a poking portion and a non-circular section are arranged at a front end of the plunger, and the non-circular section is assembled corresponding to the non- circular groove arranged inside the stopping member, wherein a fastening portion is arranged at a front section of the plunger for fastening the embedding portion to make retractable movement.

Wherein a protruding portion is arranged at the stopping member corresponding to an assembling position of the rotating member, and a receiving portion of is arranged at the rotating member to receive the protruding portion of the stopping member.

Wherein at least one stopping stand is arranged at the outer edge of the stopping member corresponding to the open end of the barrel and the stopping stand is having a rear stopping portion, and at least one stopping piece is arranged at an inner edge of the barrel corresponding to the stopping stand.

Wherein a ring stopping edge is arranged at a front section of the radial rib of the plunger, and a ring stopping groove is arranged at the guiding pressure plate corresponding to the ring stopping edge for providing locking and positioning.

A sticking member is extended from the poking portion of the plunger, a sticking portion is arranged at the front end of the radial rib of the plunger for providing the sticking member to stick into, and a sticking hole is arranged at the sticking portion corresponding to the sticking member.

This invention is making the stopper of barrel and the L-shaped groove rotate from a locking state to a non-limit open state through the auto deflection device, so as to make the plunger embed with and position at the needle set and further easily make the retractable movement for a user to form a retractile syringe mechanism. And the needle set is securely assembled and positioned at the open end of the barrel, and hardly resulted unexpected phenomenon from outside temperature, such as deteriorating the suitability between the needle set and the barrel to result the needle set indentation and leakage when injecting from a sharp raise in temperatures, or overtightening the needle set and the barrel to result the needle and the needle set incapable of retracting in the barrel from the sharp fall of temperature. Furthermore, this invention is capable of achieving one hand operation with safety, improving environmental protection quantity, and easy use for retracting the needle.

Further features and advantages of the present invention will become apparent to those of skill in the art in view of the detailed description of preferred embodiments which follows, when considered together with the attached drawings and claims.

BRIEF DESCRIPTION OF THE DRAWINGS

All the objects, advantages, and novel features of the invention will become more apparent from the following detailed descriptions when taken in conjunction with the accompanying drawings.

DESCRIPTION OF THE PREFERRED EMBODIMENT

Figure 1:
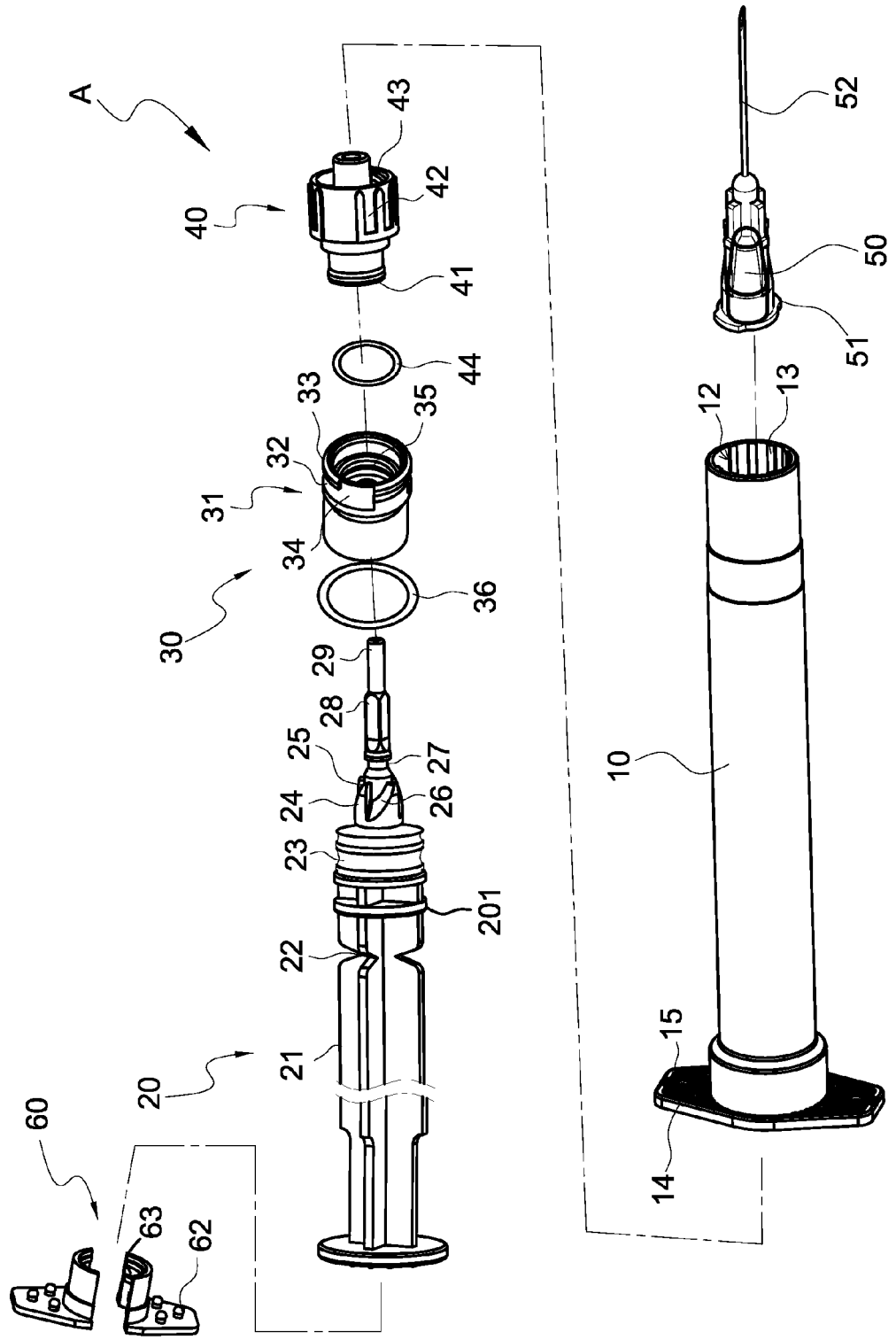
FIG. 1 shows an exploded view of the safety syringe in accordance with the invention.
Figure 2:
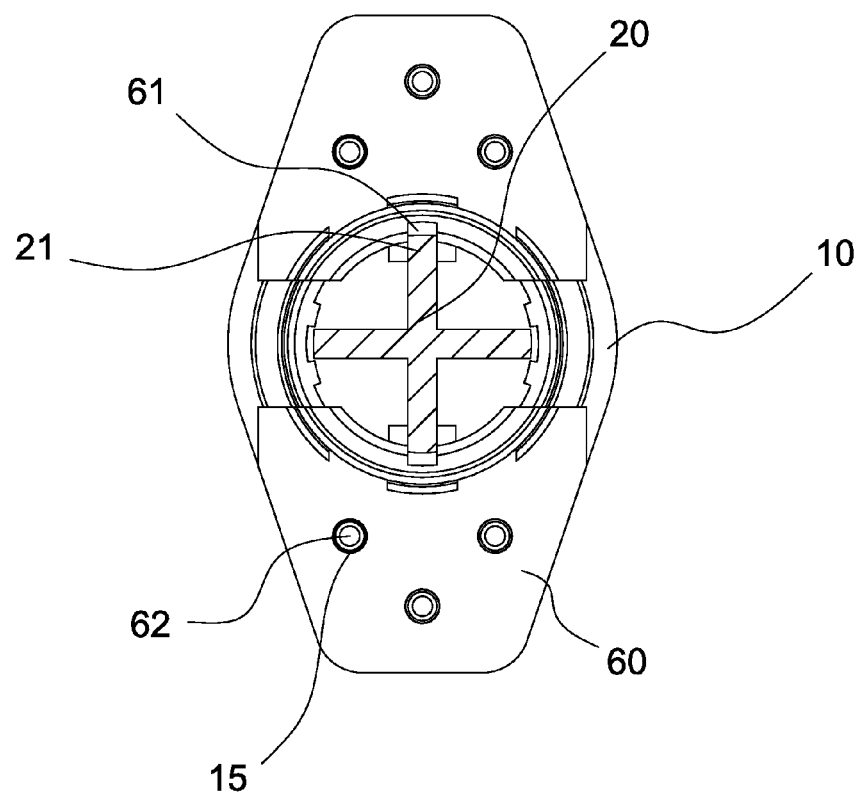
FIG. 2 shows a sectional view of a rear part of the safety syringe in accordance with the invention.

Referring now to the drawings where like characteristics and features among the various figures are denoted by like reference characters.

The preferred embodiment of this invention is disclosed a safety syringe, which is comprised a barrel 10, a needle set A, and a plunger 20.

Please refer to FIG. 1, a receiving cavity 12 is formed inside the barrel 10, and at least one stopper 11 (the quantity of the stopper 11 is two) is arranged adjacent to an open end of the receiving cavity 12. At least one stopping pieces 13 is arranged at the other side of the stoppers 11. At least one guiding pressure plate 60 is arranged at a tail end of the barrel 10, wherein the tail end is formed a holding end and a plurality of assembling holes 15 each for providing a connecting portion 62 of the guiding pressure plate 60 to assemble are passing through a predetermined position of the holding end 14. Furthermore, limit grooves 61 of each guiding pressure plate 60 are arranged corresponding to and toward the inside of the receiving cavity 12.

Figure 3:
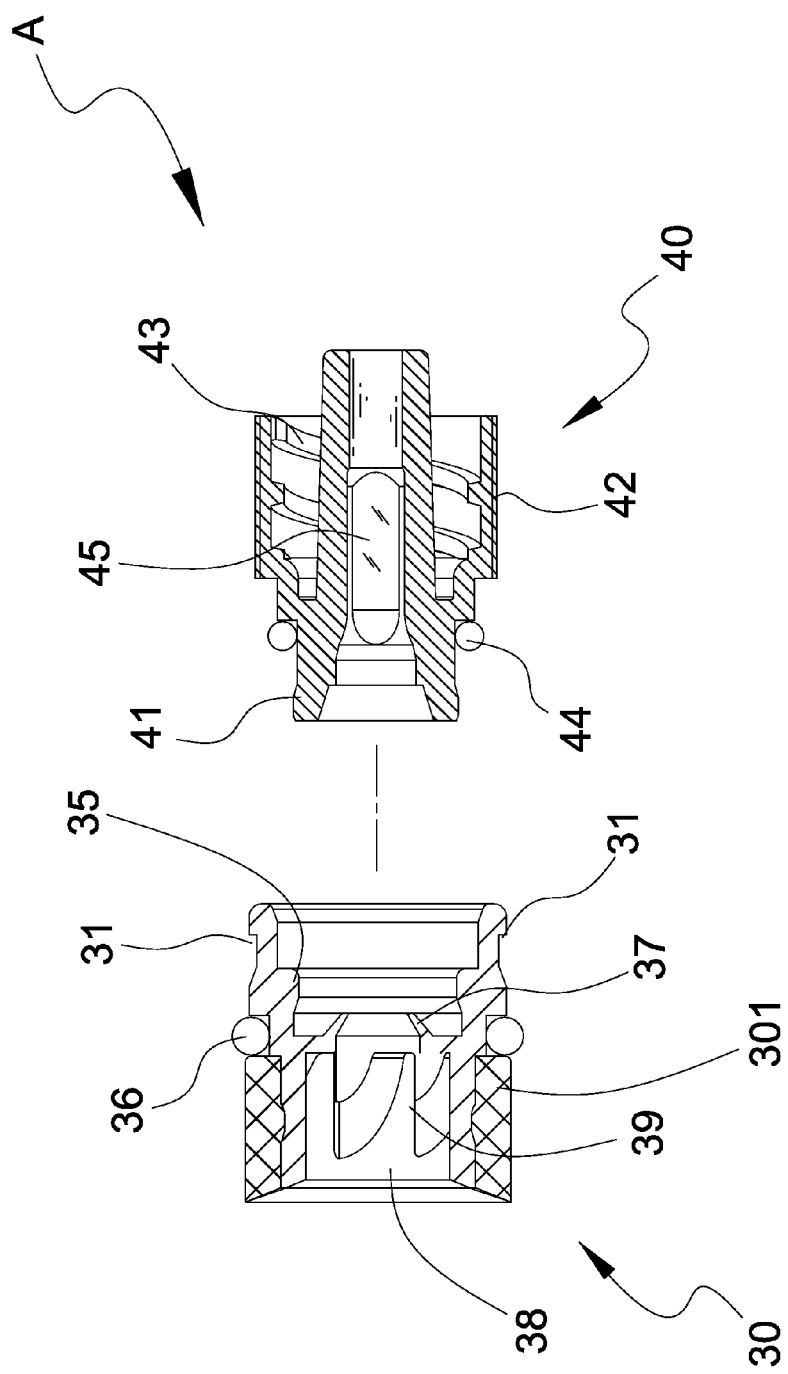
FIG. 3 shows an exploded and sectional view of the needle set in accordance with the invention.
Figure 9:
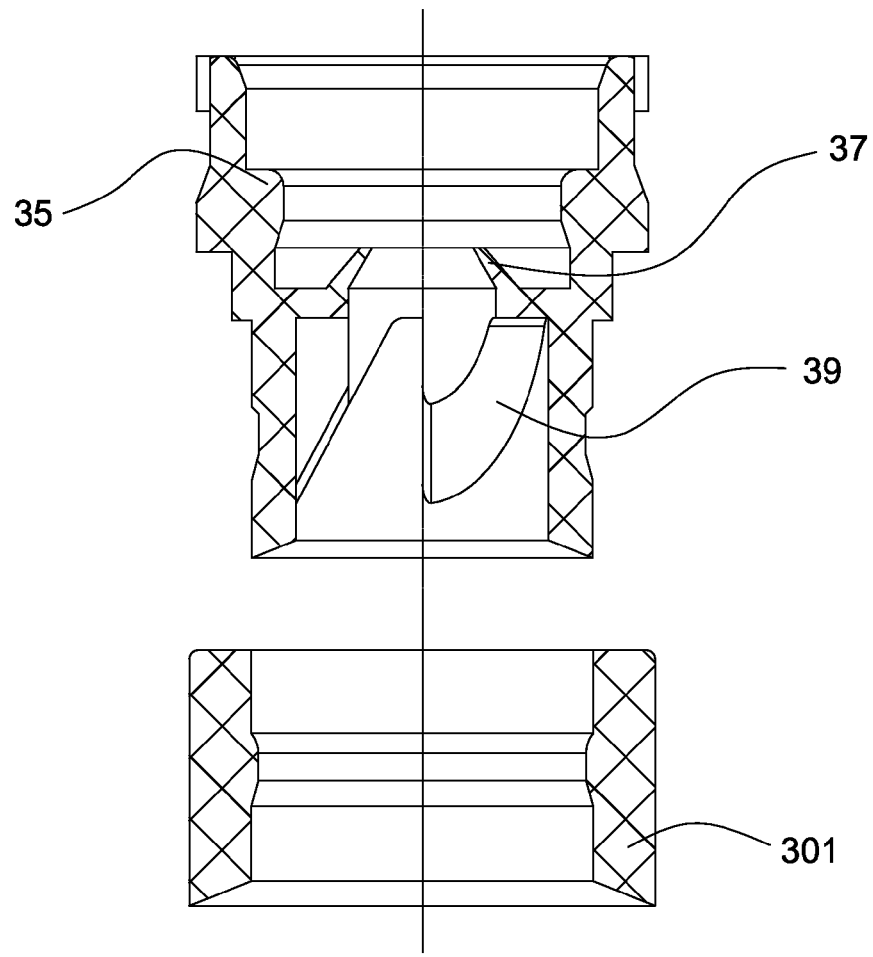
FIG. 9 shows a schematic diagram of the rotating member and the assembling member in accordance with the invention.

Please refer to FIG. 1, the needle set A is limited at the open end of the barrel 10 and comprises a rotating member 30 and stopping member 40 pivoted each other. A protruding portion 41 is arranged at the stopping member 40 corresponding to an assembling position of the rotating member 30. A receiving portion 35 is arranged at the rotating member 30 corresponding to the protruding portion 41, so that the rotating member 30 is capable of engaging with the stopping member 40. A sealing ring 44 is arranged at the pivoting position between the rotating member 30 and the stopping member 40. Please refer to FIGS. 3, 4, and 9, an assembling member 301 is arranged at a rear end of the rotating member 30 for embedding with the rotating member 30, and a sealing ring 36 is arranged at a gap therebetween corresponding to the barrel 10.

In addition, the rotating member 30 and the stopping member 40 are having an auto deflection device respectively. Please refer to FIG. 3, the auto deflection device comprises a rotated portion 38 arranged inside the rotating member 30 and a non-circular groove 45 arranged at a predetermined position inside the stopping member 40, wherein a guiding inclined plane 39 is formed in the rotated portion 38. Furthermore, an embedding portion 37 is arranged at the other side of the rotating member 30 with the rotated portion 38. The L-shaped groove 31 is arranged at an outer ring edge of the rotating member 30 and includes a lateral close end 32 and an axial open end 34, wherein a stopping portion 33 is arranged at one side of the close end 32. The L-shaped groove 31 is having the function of limiting-to-lock or nonlimiting-to-open to the stopper 11 of the barrel 10 through a deflection angle of the rotating member 30.

Figure 4:
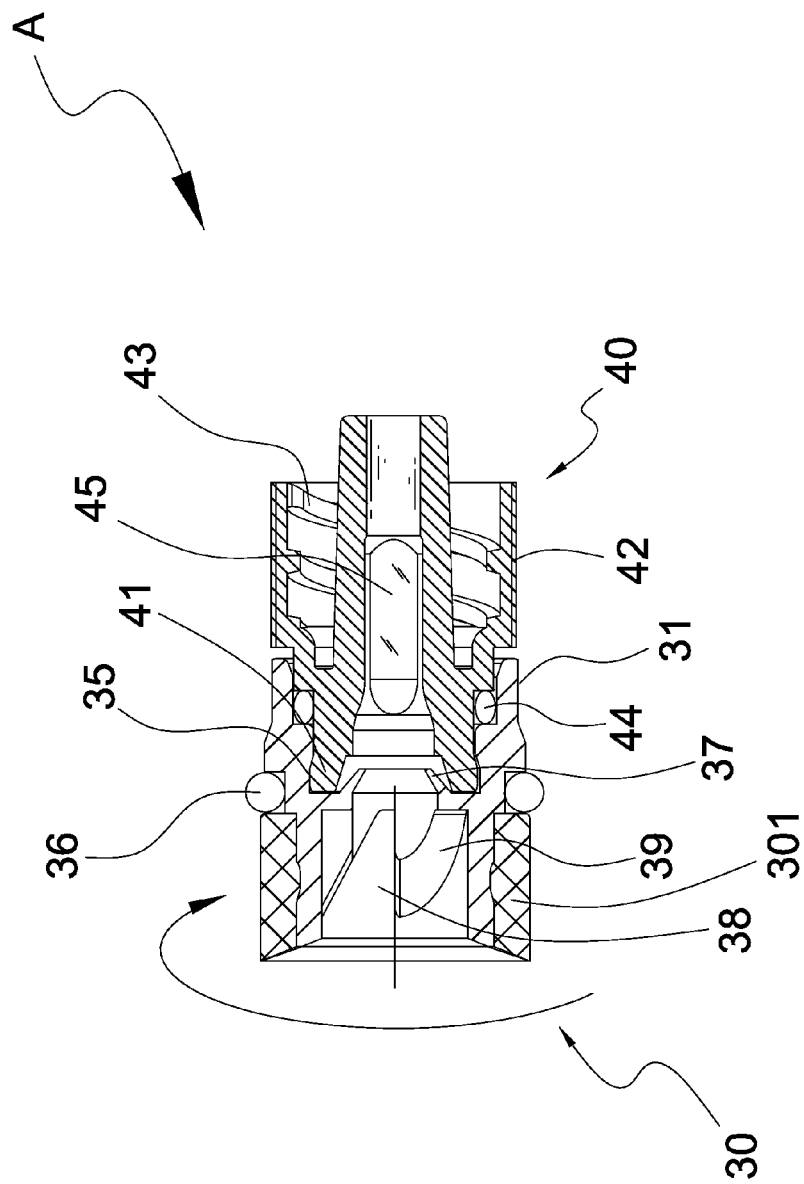
FIG. 4 shows a structured diagram of the needle set in accordance with the invention.

Please refer to FIG. 4, at least one stopping stand 42 for limiting to push forward is arranged at an outer edge of the stopping member 40 corresponding to the open end of the barrel 10. At least one stopping piece 13 is arranged at an inner edge of the barrel 10 corresponding to the stopping stand 42. The stopping stand 42 is including a rear stopping portion. Each stopping stand 42 of the stopping member 40 is staggering the stoppers 11 inside the cavity 12 of the barrel 10, so that the rear stopping portion of the stopping stand 42 is capable of embedding and limiting smoothly at the stopping piece 13 of the barrel 10 while the stopping member 40 is assembled to the open end of the barrel 10. An assembling portion 43 with an inside thread is formed in front of the stopping member 40 for providing to screw with an assembling tail end 51 of a replaceable injecting member 50, wherein a metal injection needle 52 is arranged at a front end of the injecting member 50.

Please refer to FIG. 1, the front section of the plunger 20 is in series comprising a poking portion 24, a fastening portion 27, a non-circular section 28, and a front guiding post 29. And the rear section of the plunger 20 comprises a radial rib 21 with radial cross-section. A ring stopping edge 201 and a rubber plug 23 are arranged at the front section of the radial rib 21, and one rib of the radial ribs 21 is capable of passing through and being guided by the limit groove 61 of the guiding pressure plate 60 to form a linear track, so that the plunger 20 is only making straight line back-and-forth movement. And a cutting notch 22 is arranged at a predetermined position of the radial rib 21 so as to be cut by a user. A ring stopping groove 63 is arranged at the guiding pressure plate 60 and providing to stop and limit. Please also refer to FIG. 5, the non-circular section 28 of the plunger 20 is capable of assembling to the non-circular groove 45 of the stopping member 40. After the non-circular section 28 is assembling to the non-circular groove 45, the radial rib 21 is making back-and-forth movement corresponding to the limit groove 61 and the plunger 20 is moving with its own axis. And further the poking portion 24 of the plunger 20 is poking the rotated portion 38 of the rotating member 30, so that the rotating member is making auto deflection movement. An inclined groove 26 is arranged at the poking portion 24 and a poking end 25 is arranged at the front of the poking portion 24. The poking end 25 is for providing to guide and contact the guiding inclined plane 30, so that the rotating member 30 is performing auto deflection and releasing the locking mode of the needle set A and the barrel 10 while the plunger 20 is straightly moved into the barrel 10. In addition, the fastening portion 27 of the plunger 20 is for fastening the embedding portion 37 to make retractile movement in safety.

Figure 8:
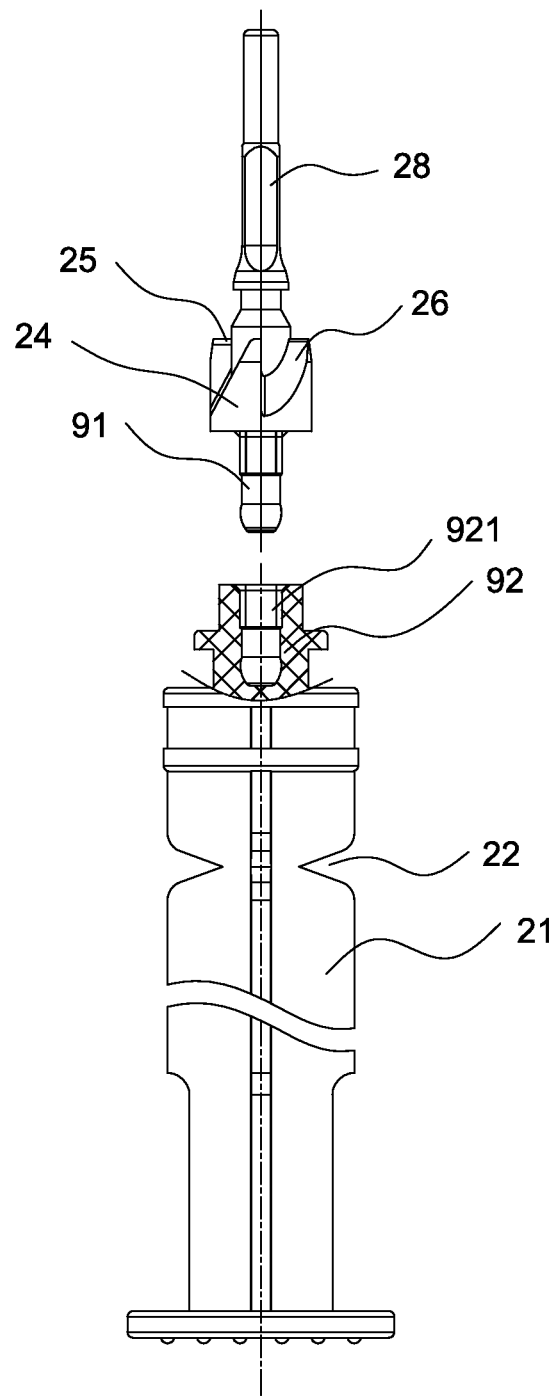
FIG. 8 shows a schematic diagram of a separate structure of the plunger in accordance with the invention.

Please refer to FIG. 8, the plunger of this invention is capable of being connected by separate parts. A sticking member 91 is extended from the poking portion 24 of the plunger 20. A sticking portion 92 is arranged at the front end of the radial rib 21 of the plunger 20 for providing the sticking member 91 to stick into, and a sticking hole 921 is arranged at the sticking portion 92 corresponding to the sticking member 91. The front section of the plunger 20, which is comprised of the poking portion 24, the fastening portion 27, the non-circular section 28, and the front guiding post 29, and the rear section of the plunger 20 are arranged in on-axis or off-axis. The front end and the rear end of the plunger 20 are arranged in off-axis to further adapt to use for a volume which is larger than or equal to 20 c.c.

Figure 5:
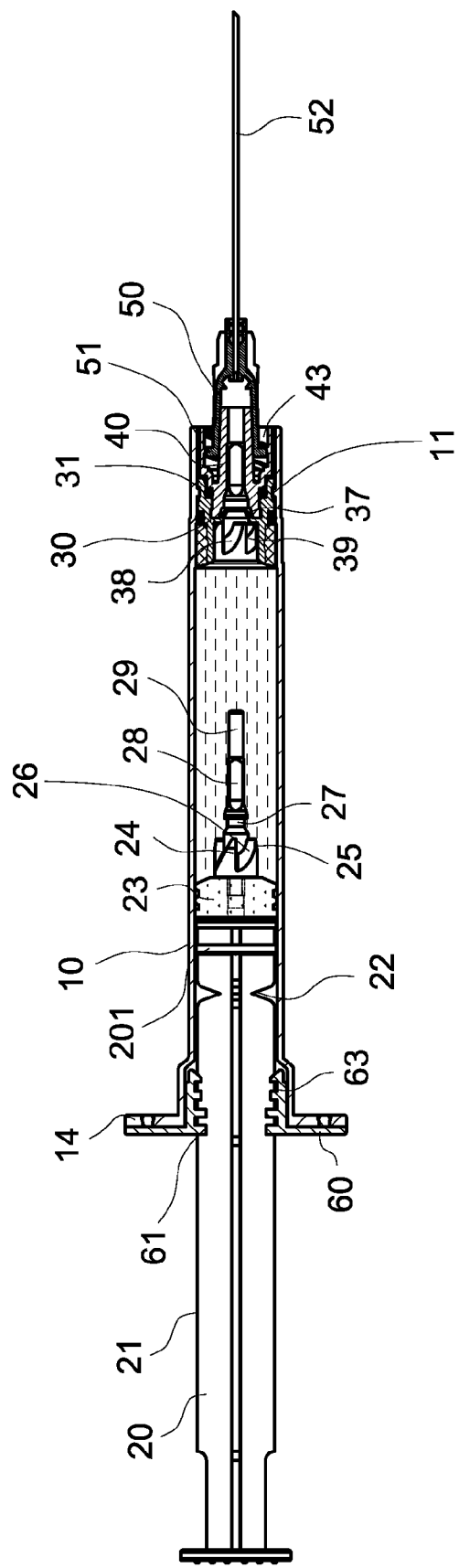
FIG. 5 shows a schematic diagram of the safety syringe, wherein the syringe is in an uninjected state.
Figure 6:
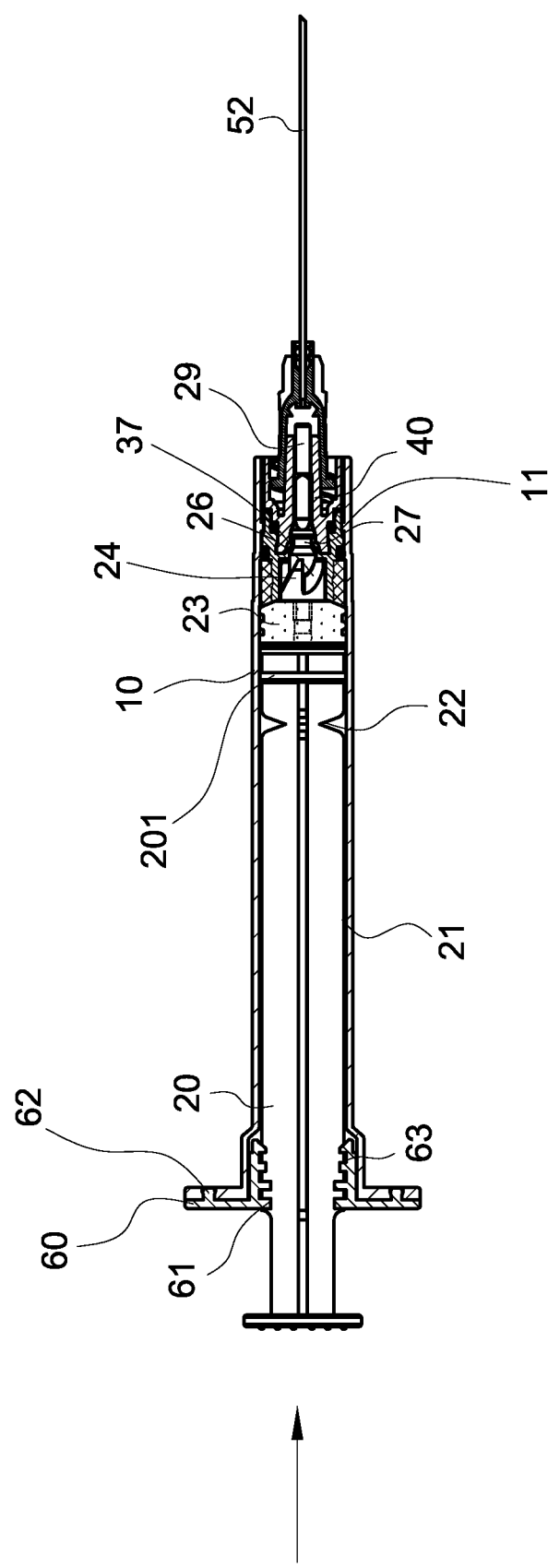
FIG. 6 shows a schematic diagram of the safety syringe in accordance with the invention, wherein the syringe is in an injected state.
Figure 7:
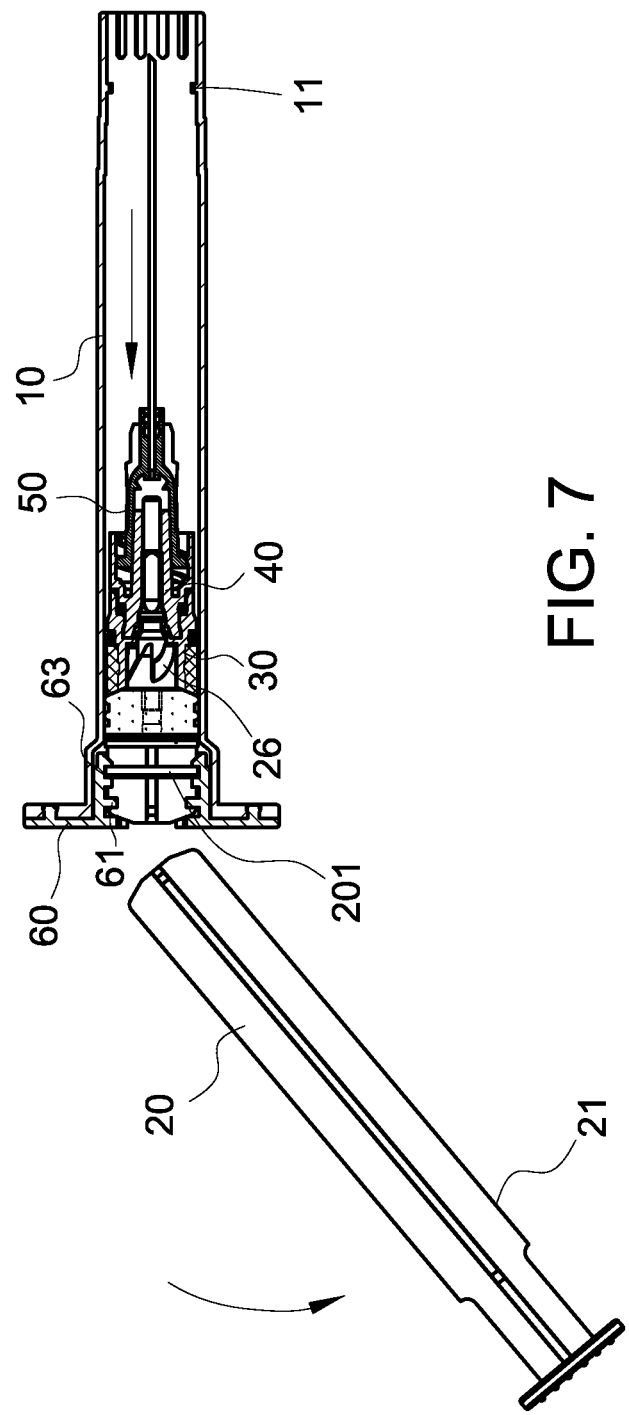
FIG. 7 shows a schematic diagram of the safety syringe in accordance with the invention, wherein the plunger is in an break-off state after refracting.

Please refer to FIG. 5 to FIG. 7, the needle set A is normally using the stopping stand 42 of the stopping member 40 to arrange at the stopping piece 13, and using the stopping portion 33 arranged at the close end 32 of the L-shaped groove 31 to align with the stopper 11 of the barrel 10, so that the rotating member 30, stopping member 40, and the barrel 10 are locked one another in a locking mode.

The detail operation of the safety syringe of this invention is described as below. Firstly, the plunger 20 is pushed forward to a suitable position which is a non-fastening position between the fastening portion 27 of the plunger 20 and the embedding portion 37 of the rotating member 30. Secondly, the injection needle 52 is stuck in a liquid medicine bottle and the plunger 20 is pulled back to make the barrel 10 become vacuum, so that the liquid medicine is infused to the barrel 10 with the vacuum till the required volume is achieved, and then, the syringe is separated from the medicine bottle. If a mix of medicines is needed, the liquid medicine is injected to the powder bottle directly and then infused back to the syringe after mixing well. The injecting member 50 is replaced a finer needle 52, the barrel 10 is tapped, and the plunger 20 is slowly pushed forward, so that the air in the barrel 10 is exhausted and the over liquid medicine is discharged.

Because the stopping stand 42 of the stopping member 40 is arranged at the stopping piece 13 inside the receiving cavity 12 of the barrel 10 and the stopping portion 33 is arranged at the close end 32 of the L-shaped groove 31 to align with the stopper 11 of the barrel 10, the leak quality of the syringe is able to be held while replacing the injecting member 50 and the needle 52 is capable of securely positioning and smoothly injecting to human skin.

The non-circular section 28 of the plunger 20 is assembled to the non-circular groove 45 of the stopping member 40, the stopping stand 42 of the stopping member 40 is embedded with the stopping piece 13 of the barrel 10, and the radial rib 21 of the plunger 20 is led linearly by the limit groove 61 of the guiding pressure plate 60, so that the plunger 20 is making back-and-forth movement straightly and without deflection while injecting. When the poking portion 24 of the plunger 20 is gradually contacting the guiding inclined plane 39 of the rotated portion 38 of the rotating member 30, the rotating member 30 is moved back-and-forth straightly by the plunger 20, so that the rotating member 30 is corrected to a predetermined angle after forcing, the open end 34 of the L-shaped groove 31 is aligned with the stopper 11 of the barrel, the stopper 11 of the barrel 10 is not limited and locked anymore by the stopping portion 33, and the needle set A is in a retractile open mode. Meanwhile, the fastening portion 27 of the plunger 20 is pushed forward and fastened at the embedding portion 37 of the rotating member 30, so that the plunger 20 is further leading the needle set A to make a retractile movement and the needle set and the needle 52 are all getting into the barrel 10. After the ring stopping edge 201 is positioned at the ring stopping groove 63 of the guiding pressure plate 60, the cutting notch 22 of the plunger 20 is exposed and a user is able to break off the cutting notch 22 of the plunger 20 to prevent the syringe from reusing.

Hereby, this invention is using the auto deflection device of the needle set to make the groove of the needle set and the stopper of the barrel from a limiting locking state rotate to a non-limiting open state, so that the plunger 20 is capable of rapidly embedding with and positioning at the needle set A, the next step of the retractile movement to retract the needle 52 is easily processed by a user, and the needle set A is firmly assembled and positioned at the open end of the barrel 10 so as to not easily result an unpredictable phenomenon, such as deteriorating the suitability between the needle set and the barrel to result the needle set indentation and leakage when injecting from a sharp raise in temperatures, or overtightening the needle set and the barrel to result the needle and the needle set incapable of retracting in the barrel from the sharp fall of temperature. Furthermore, this invention is capable of achieving one hand operation with safety, improving environmental protection quantity, and easy use for retracting the needle.

Although the invention has been explained in relation to its preferred embodiment, it is not used to limit the invention. It is to be understood that many other possible modifications and variations can be made by those skilled in the art without departing from the spirit and scope of the invention as hereinafter claimed.

What is claimed is:

1. A safety syringe with retractable rotation, the safety syringe comprising:
    a barrel, having a receiving cavity formed in the barrel, at least one stopper arranged at an open end of the receiving cavity, and at least one guiding pressure plate arranged at a tail end of the barrel, wherein limit grooves of said guiding pressure plate are arranged corresponding to and toward an inner portion of the receiving cavity;
    a needle set, limited at the open end of the barrel and including a rotating member and a stopping member engaged with each other, wherein an auto deflection device is disposed between the rotating member and the stopping member, and the auto deflection device has a rotated portion arranged inside the rotating member and a non-circular groove arranged at a predetermined position inside the stopping member, and an embedding portion is arranged at an end of the rotating member relative to the rotated portion, wherein at least one L-shaped groove is arranged at an outer ring edge of the rotating member for limiting and aligning with the stopper of the barrel so that the rotating member, stopping member and the barrel are locked with each other in a locking mode, and an assembling member is arranged at a rear end of the rotating member for embedding with the rotating member; and
    a plunger, having at least one radial rib arranged at outer edge, wherein the radial rib is guided by the limit groove of the guiding pressure plate and formed a linear track, wherein a poking portion and a non-circular section are arranged at a front end of the plunger, and the non-circular section is assembled corresponding to the non-circular groove arranged inside the stopping member, so that the plunger is only allowed to move linearly, and when the plunger is pushed forward, an inclined groove arranged at the poking portion engages and exerts force to a guiding inclined plane of the rotating member to separate the L-shaped groove of the rotating member with the stopper of the barrel to release the locking mode between the rotating member, stopping member and the barrel.

2. The safety syringe as claimed in claim 1, wherein a protruding portion is arranged at the stopping member corresponding to an assembling position of the rotating member, and a receiving portion is arranged at the rotating member to receive the protruding portion of the stopping member.

3. The safety syringe as claimed in claim 1, wherein at least one stopping stand is arranged at an outer edge of the stopping member corresponding to the open end of the barrel and the stopping stand that has a rear stopping portion, and at least one stopping piece is arranged at an inner edge of the barrel corresponding to the stopping stand.

4. The safety syringe as claimed in claim 1, wherein a ring stopping edge is arranged at a front section of the radial rib of the plunger, and a ring stopping groove is arranged at the guiding pressure plate corresponding to the ring stopping edge to provide locking and positioning.

5. The safety syringe as claimed in claim 3, wherein a ring stopping edge is arranged at a front section of the radial rib of the plunger, and a ring stopping groove is arranged at the guiding pressure plate corresponding to the ring stopping edge to provide locking and positioning.

6. The safety syringe as claimed in claim 1, wherein a sticking member extends from the poking portion of the plunger, a sticking portion is arranged at the front end of the radial rib of the plunger for providing the sticking member to stick into, and a sticking hole is arranged at the sticking portion corresponding to the sticking member.

7. The safety syringe as claimed in claim 3, wherein a sticking member extends from the poking portion of the plunger, a sticking portion is arranged at the front end of the radial rib of the plunger for providing the sticking member to stick into, and a sticking hole is arranged at the sticking portion corresponding to the sticking member.

8. The safety syringe as claimed in claim 4, wherein a sticking member extends from the poking portion of the plunger, a sticking portion is arranged at the front end of the radial rib of the plunger for providing the sticking member to stick into, and a sticking hole is arranged at the sticking portion corresponding to the sticking member.

9. The safety syringe as claimed in claim 5, wherein a sticking member extends from the poking portion of the plunger, a sticking portion is arranged at the front end of the radial rib of the plunger for providing the sticking member to stick into, and a sticking hole is arranged at the sticking portion corresponding to the sticking member.

10. The safety syringe as claimed in claim 1, wherein a fastening portion is arranged at a front section of the plunger for fastening the embedding portion to make retractile movement.

* * * * *